(12) United States Patent
Tung et al.

(10) Patent No.: US 11,779,375 B2
(45) Date of Patent: Oct. 10, 2023

(54) DEVICE AND METHOD FOR EXPANDING SPACING BETWEEN SPINOUS PROCESSES

(71) Applicant: Megaspine Medical Co., Ltd., New Taipei (TW)

(72) Inventors: Jung-Tsou Tung, New Taipei (TW); Chang-Yi Kuo, New Taipei (TW); Te-Jung Li, New Taipei (TW); Chi-Yen Yang, New Taipei (TW); Chia-Jui Lo, New Taipei (TW); Hao-Yun Tung, New Taipei (TW)

(73) Assignee: MEGASPINE MEDICAL CO., LTD., New Taipei (TW)

( * ) Notice: Subject to any disclaimer, the term of this patent is extended or adjusted under 35 U.S.C. 154(b) by 0 days.

(21) Appl. No.: 17/839,629

(22) Filed: Jun. 14, 2022

(65) Prior Publication Data

US 2022/0401134 A1 Dec. 22, 2022

(30) Foreign Application Priority Data

Jun. 16, 2021 (TW) .................. 110121818

(51) Int. Cl.
*A61B 17/70* (2006.01)
*A61B 17/56* (2006.01)
*A61B 17/68* (2006.01)

(52) U.S. Cl.
CPC .... *A61B 17/7065* (2013.01); *A61B 2017/564* (2013.01); *A61B 2017/681* (2013.01)

(58) Field of Classification Search
CPC ............ A61B 17/7065; A61B 17/7067; A61B 17/7068; A61B 17/707; A61B 17/7062
See application file for complete search history.

(56) References Cited

U.S. PATENT DOCUMENTS

| 8,292,923 | B1 * | 10/2012 | Arnold | A61B 17/7062 606/249 |
| 9,017,383 | B2 * | 4/2015 | Ciupik | A61B 17/7065 606/105 |
| 9,707,017 | B2 * | 7/2017 | Ciupik | A61B 17/7065 |
| 2005/0261768 | A1 * | 11/2005 | Trieu | A61B 17/7065 623/17.11 |
| 2008/0177271 | A1 * | 7/2008 | Yeh | A61B 17/7065 606/90 |

(Continued)

*Primary Examiner* — Jan Christopher L Merene
*Assistant Examiner* — Anna V. Little
(74) *Attorney, Agent, or Firm* — Locke Lord LLP; Tim Tingkang Xia, Esq.

(57) ABSTRACT

A device for expanding spacing between spinous processes includes a first supporter, a second supporter and a pin. The first supporter includes a first protrusion, a second protrusion opposing the first protrusion, and a first concave portion formed between the first protrusion and the second protrusion for supporting one spinous process. The second supporter includes a third protrusion, a fourth protrusion opposing the third protrusion, and a second concave portion formed between the third protrusion and the fourth protrusion for supporting another spinous process. The pin pivots the first supporter to the second supporter so as to provide the device an expansion state and a close state for removal and installation between two spinous processes. In addition, a method for expanding spacing between spinous processes is also provided.

24 Claims, 17 Drawing Sheets

(56) References Cited

U.S. PATENT DOCUMENTS

| | | | |
|---|---|---|---|
| 2008/0208344 A1* | 8/2008 | Kilpela | A61F 2/442 623/17.11 |
| 2009/0138046 A1* | 5/2009 | Altarac | A61B 17/7076 623/17.11 |
| 2009/0149886 A1* | 6/2009 | Zentes | A61B 17/7065 606/86 A |
| 2010/0179595 A1* | 7/2010 | Jackson | A61B 17/7065 606/86 A |
| 2016/0015432 A1* | 1/2016 | Northcutt | A61B 17/7062 606/249 |
| 2018/0078288 A1* | 3/2018 | Omar-Pasha | A61B 17/707 |

* cited by examiner

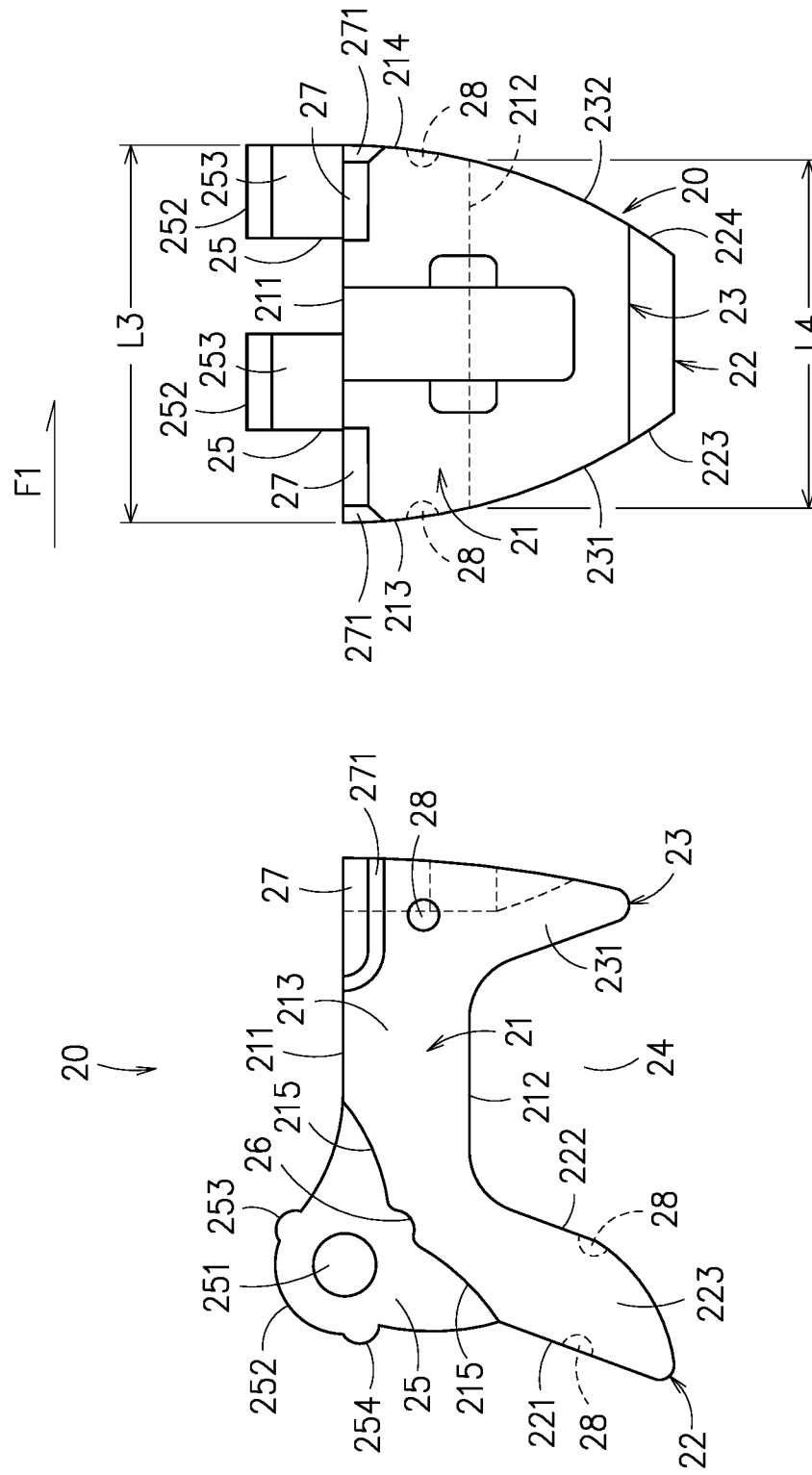

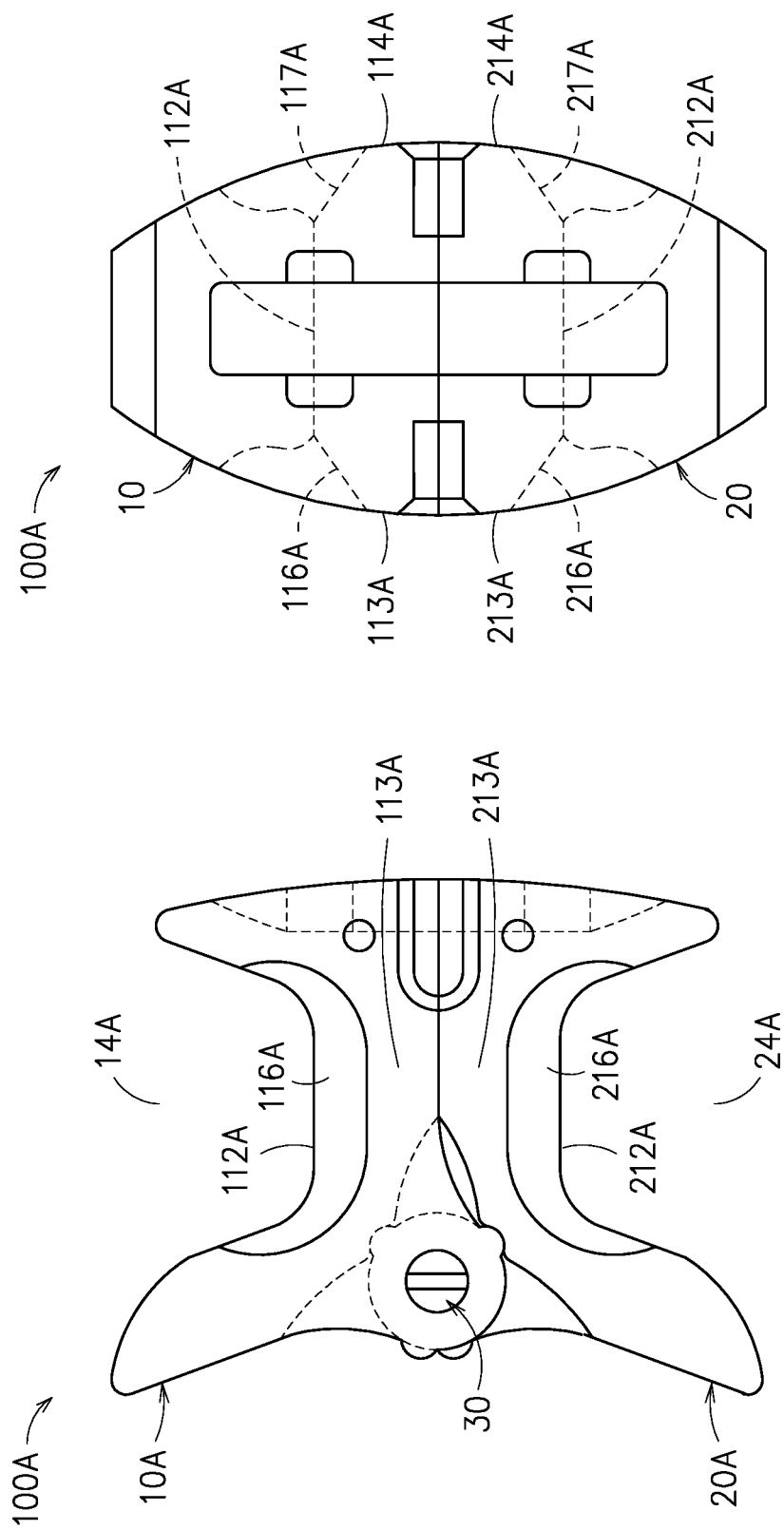

DEVICE AND METHOD FOR EXPANDING SPACING BETWEEN SPINOUS PROCESSES

CROSS REFERENCE TO RELATED APPLICATION

This application claims the benefits of Taiwan application Serial No. 110121818, filed on Jun. 16, 2021, the disclosures of which are incorporated by references herein in its entirety.

TECHNICAL FIELD

The present disclosure relates in general to an field of medical technology, and more particularly to a device and method for expanding spacing between spinous processes.

BACKGROUND

For patients with spinal disorders, lesions and/or atrophy would be easily developed at the intervertebral discs, from which narrowing in spacing of spinal process would lead to possible compression of related spinal nerves, and further to result in paralysis or pain.

In order to solve the aforesaid problem, conventional treatment methods such as implantation of supporters, pedicle screws or artificial intervertebral disc fillers, are introduced to displace the intervertebral processes so as to enlarge the corresponding neuroforaminal space, and thus to reduce or eliminate discomfort of the patient.

In particular, as far as the currently used supporters are concerned, the use of some supports shall firstly destroy the spinal ligament during installation. Such an application, defects including complex structuring, difficult operation, difficulty in both installation and removal, and so on are inevitable. As a result, a related surgery would be time-consuming, and the risk of bleeding and infection shall not be ignored.

Accordingly, it is urge to a person having ordinary skill in the art to develop a "device and method for expanding spacing between spinous processes" that is simply structured, easily operated, simply installed and removed, and able to retain the ligament of spinous process and maintain the cone stability.

SUMMARY

In one embodiment of this disclosure, a device for expanding spacing between spinous processes comprise:
a first supporter, including:
a first body, having oppositely a first surface and a second surface;
a first protrusion, protruding at one side of the second surface;
a second protrusion, protruding at another side of the second surface by opposing the first protrusion;
a first concave portion, formed among the second surface, the first protrusion and the second protrusion;
a second supporter, including:
a second body, having oppositely a third surface and a fourth surface;
a third protrusion, protruding at one side of the fourth surface;
a fourth protrusion, protruding at another side of the fourth surface by opposing the third protrusion; and
a second concave portion, formed among the fourth surface, the third protrusion and the fourth protrusion; and
a pin, disposed pivotally at the first supporter and the second supporter, the first supporter and the second supporter pivoting about the pin to provide the device for expanding spacing between spinous processes an expansion state and a close state; wherein, while the device for expanding spacing between spinous processes in the expansion state, the first protrusion and the third protrusion are contacted to each other; wherein, while the device for expanding spacing between spinous processes in the close state, the first surface and the third surface are contacted to each other.

In one embodiment of this disclosure, a method for expanding spacing between spinous processes comprises the steps of:
(a) preparing a device for expanding spacing between spinous processes, the device including:
a first supporter, including:
a first body, having oppositely a first surface and a second surface;
a first protrusion, disposed at a side of the second surface;
a second protrusion, disposed at another side of the second surface by opposing the first protrusion; and
a first concave portion, formed on the second surface between the first protrusion and the second protrusion;
a second supporter, including:
a second body, having oppositely a third surface and a fourth surface;
a third protrusion, disposed at a side of the fourth surface;
a fourth protrusion, disposed at another side of the fourth surface by opposing the third protrusion; and
a second concave portion, formed on the fourth surface between the third protrusion and the fourth protrusion; and
a pin, pivotally engaging the first supporter and the second supporter, the first supporter being pivotally rotated with respect to the second supporter via the pin;
(b) turning the first supporter and the second supporter to have the first protrusion to contact the third protrusion, so that the first supporter and the second supporter are posed in an expansion state;
(c) inserting the first protrusion of the first supporter and the third protrusion of the second supporter into a space between two spinous processes;
(d) turning the first supporter and the second supporter to have the first surface to contact the third surface, so that the first supporter and the second supporter are posed in a close state; and
(e) having the first protrusion and the third protrusion to dispose at a side of the two spinous processes, the second protrusion and the fourth protrusion to dispose at another side of the two spinous processes, and the first concave portion and the second concave portion to dispose between the two spinous processes.

Further scope of applicability of the present application will become more apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The present disclosure will become more fully understood from the detailed description given herein below and the accompanying drawings which are given by way of illustration only, and thus are not limitative of the present disclosure and wherein:

FIG. 4A is a schematic front view of the second supporter of FIG. 1;

FIG. 4B is a schematic right-side view of FIG. 4A;

FIG. 11A is a schematic front view of FIG. 11;

FIG. 11B is a schematic right-side view of FIG. 11;

DETAILED DESCRIPTION

Figure 1:
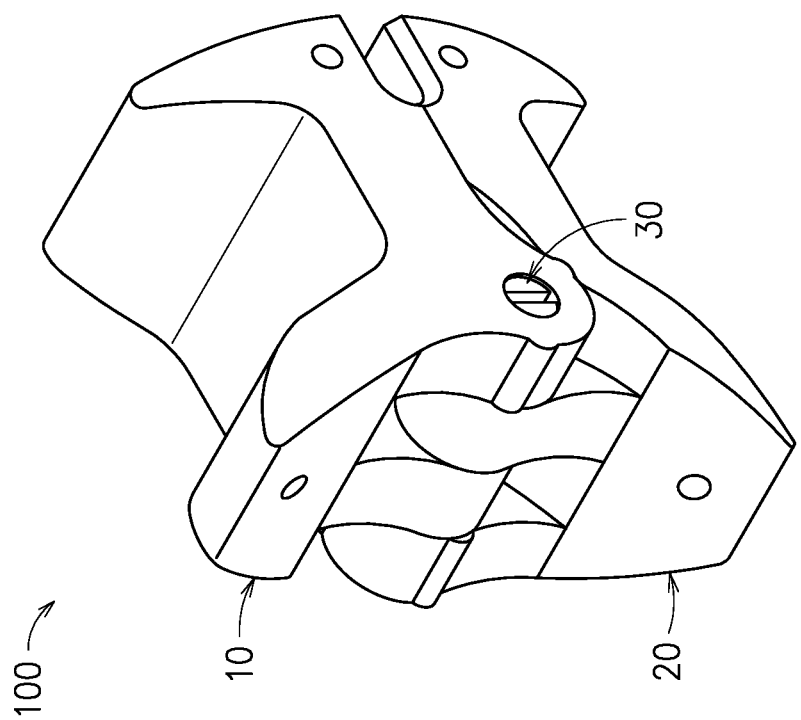
FIG. 1 is a schematic perspective view of an embodiment of the device for expanding spacing between spinous processes in accordance with this disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Figure 2:
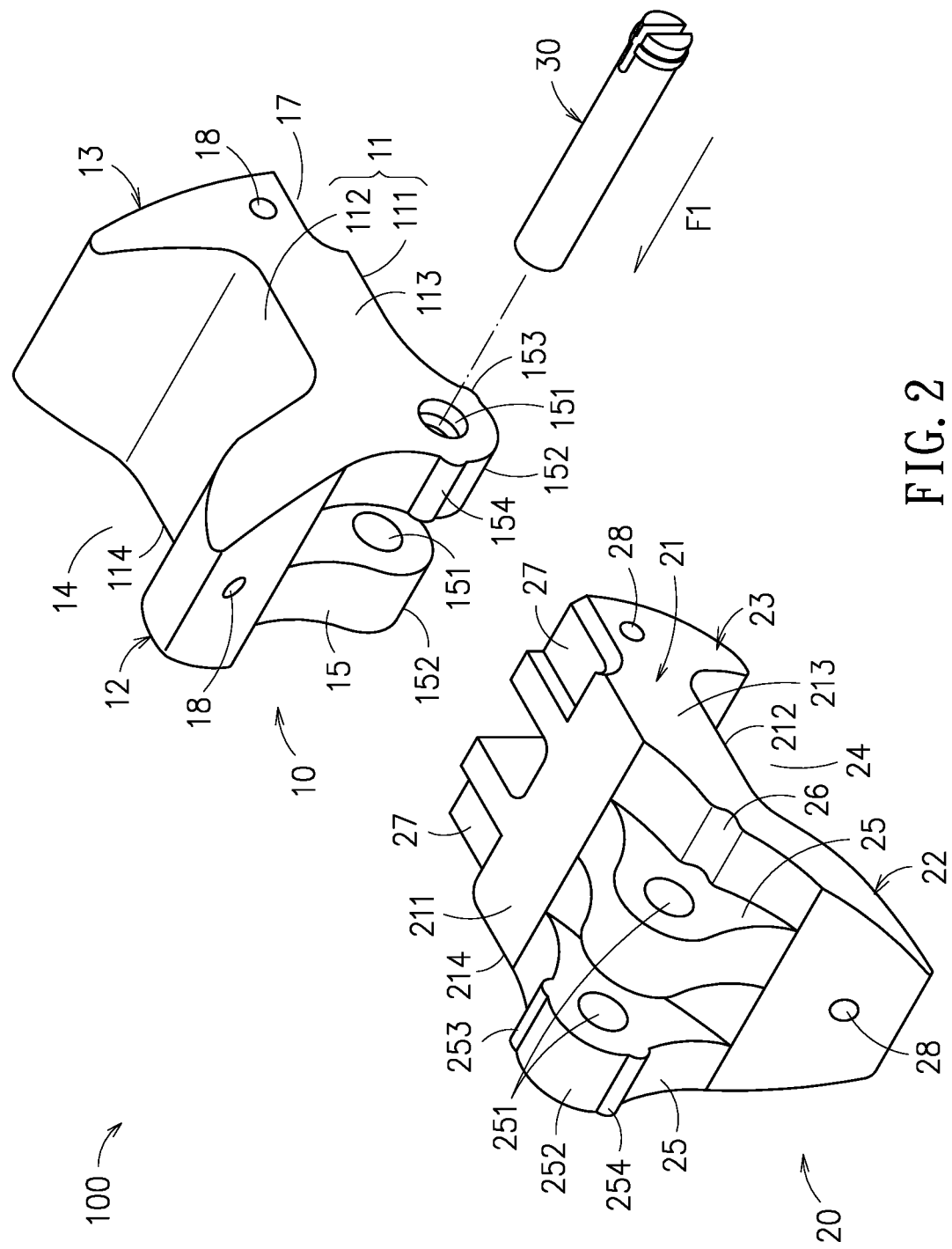
FIG. 2 is a schematic exploded view of FIG. 1.

Referring to FIG. 1 and FIG. 2, a device for expanding spacing between spinous processes 100 in accordance with this disclosure includes a first supporter 10, a second supporter 20 and a pin 30. Materials for the first supporter 10, the second supporter 20 and the pin 30 are not particularly limited to bio-compatible metals or plastics. The pin 30 has an axial direction F1.

Figure 3B:
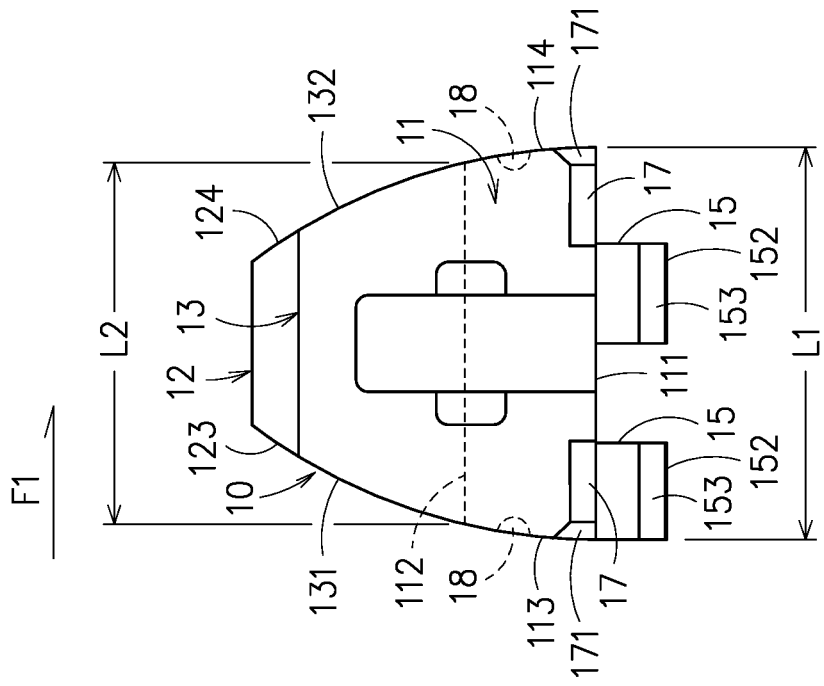
FIG. 3B is a schematic right-side view of FIG. 3A.
Figure 3A:
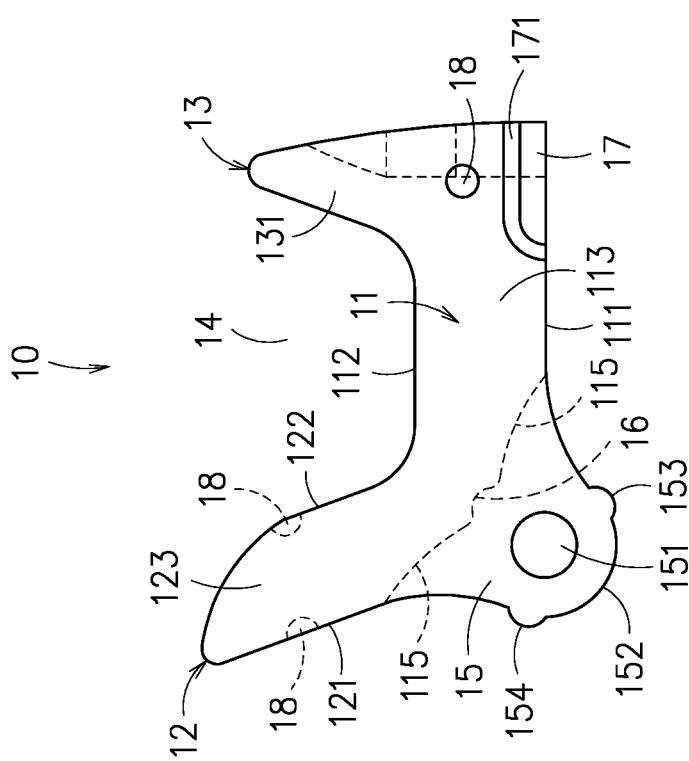
FIG. 3A is a schematic front view of the first supporter of FIG. 1.

Referring to FIG. 2, FIG. 3A and FIG. 3B, the first supporter 10 includes a first body 11, a first protrusion 12, a second protrusion 13 and a first concave portion 14.

The first body 11 has oppositely a first surface 111 and a second surface 112, and oppositely a fifth surface 113 and a sixth surface 114. The fifth surface 113 and the sixth surface 114 are disposed between the first surface 111 and the second surface 112. The fifth surface 113 and the sixth surface 114 are roughly perpendicular to the first surface 111 and the second surface 112. A width L1 of the first surface 111 between the fifth surface 113 and the sixth surface 114 is greater than a width L2 of the second surface 112 between the fifth surface 113 and the sixth surface 114. In addition, the fifth surface 113 and the sixth surface 114 are curve surfaces disposed symmetrically to each other. The width L1 is ranged within 5~20 mm, and particularly determined according to practical spacing between the two spinous processes.

The first protrusion 12, roughly shaped as a trapezoid, is protrusive at one side of the second surface 112, and a free end of the first protrusion 12 away from the second surface 112 is narrower. The second protrusion 13, oppositely disposed to the first protrusion 12 and roughly shaped as a trapezoid, is protrusive at another side of the second surface 112, and a free end of the second protrusion 13 away from the second surface 112 is narrower. The first concave portion 14 is formed above the second surface 112 and between the first protrusion 12 and the second protrusion 13.

Referring to FIG. 3A and FIG. 3B, a surface 123 connecting the first protrusion 12 and the fifth surface 113, a surface 124 connecting the first protrusion 12 and the sixth surface 114, a surface 131 connecting the second protrusion 13 and the fifth surface 113, and a surface 132 connecting the second protrusion 13 and the sixth surface 114 are all curve surfaces having curvatures roughly the same as that of the fifth surface 113 or the sixth surface 114. As shown in FIG. 3B, the two opposite surfaces 123, 124 with respect to the first protrusion 12, and the two opposite surfaces 131, 132 with respect to the second protrusion 13 are connected with the fifth surface 113 and the sixth surface 114 to form a continuous curve surface.

The first protrusion 12 and the second protrusion 13 are both protruded from the second surface 112 individually in a tapering manner. In this embodiment, the first protrusion 12 and the second protrusion 13 are identically structured to have the same curvatures, and to present a bullet shape.

Referring to FIG. 3A and FIG. 3B, the first supporter 10 further includes two first grooves 17 disposed at a side of the first body 11 by opposing the pin 30 disposed at another side thereof. These two first grooves 17 are arranged to two opposite corners of the first surface 111, and parallel to each other, but both extend in a direction perpendicular to an axial direction F1 of the pin 30. In addition, each of the two first grooves 17 is structured to provide a first chamfered edge 171 to connect the first surface 111.

Referring to FIG. 2, FIG. 4A and FIG. 4B, the second supporter 20 includes a second body 21, a third protrusion 22, a fourth protrusion 23 and a second concave portion 24.

The second body 21 has oppositely a third surface 211 and a fourth surface 212, and oppositely a seventh surface 213 and an eighth surface 214. The seventh surface 213 and the eighth surface 214 are disposed between the third surface 211 and the fourth surface 212. The seventh surface 213 and the eighth surface 214 are roughly perpendicular to the third surface 211 and fourth surface 212. A width L3 of the third surface 211 between the seventh surface 213 and the eighth surface 214 is greater than a width L4 of the fourth surface 212 between the seventh surface 213 and the eighth surface 214. In addition, the seventh surface 213 and the eighth surface 214 are curve surfaces disposed symmetrically to each other. The width L3 is ranged within 5~20 mm, and particularly determined according to practical spacing between the two spinous processes. In this embodiment, the width L3 is equal to the width L1 shown in FIG. 3B.

The third protrusion 22, roughly shaped as a trapezoid, is protrusive at one side of the fourth surface 212, and a free end of the third protrusion 22 away from the fourth surface 212 is narrower. The fourth protrusion 23, oppositely disposed to the third protrusion 22 and roughly shaped as a trapezoid, is protrusive at another side of the fourth surface 212, and a free end of the second protrusion 13 away from the fourth surface 212 is narrower. The second concave portion 24 is formed above the fourth surface 212 and between the third protrusion 22 and the fourth protrusion 23.

Referring to FIG. 4A and FIG. 4B, a surface 223 connecting the third protrusion 22 and the seventh surface 213, a surface 224 connecting the third protrusion 22 and the eighth surface 214, a surface 231 connecting the fourth protrusion 23 and the seventh surface 213, and a surface 232 connecting the fourth protrusion 23 and the eighth surface 214 are all curve surfaces having curvatures roughly the same as that of the seventh surface 213 or the eighth surface 214. As shown in FIG. 4B, the two opposite surfaces 123, 124 with respect to the first protrusion 12, and the two opposite surfaces 231, 232 with respect to the fourth protrusion 23 are connected with the seventh surface 213 and the eighth surface 214 to form a continuous curve surface.

The third protrusion 22 and the fourth protrusion 23 are both protruded from the fourth surface 112 individually in a tapering manner. In this embodiment, the third protrusion 22 and the fourth protrusion 23 are identically structured to have the same curvatures, and to present a bullet shape.

Referring to FIG. 4A and FIG. 4B, the second supporter 20 further includes two second grooves 27 disposed at a side of the second body 21 by opposing the pin 30 disposed at another side thereof. These two second grooves 27 are arranged to two opposite corners of the third surface 211, and parallel to each other, but both extend in a direction perpendicular to the axial direction F1 of the pin 30. In addition, each of the two second grooves 27 is structured to provide a second chamfered edge 271 to connect the third surface 211.

Referring to FIG. 3A and FIG. 3B, the first supporter 10 is further furnished with a plurality of notches 18. As shown, a pair of these notches 18 are disposed individually to opposite surfaces 121, 122 of the first protrusion 12, where these two surfaces 121, 122 are parallel to the axial direction F1 of the pin 30. In addition, another pair of these notches 18 are disposed individually to the opposite fifth and sixth surfaces 113, 114 at corresponding positions between the second protrusion 13 and the corresponding first grooves 17.

Referring to FIG. 4A and FIG. 4B, the second supporter 20 is further furnished with a plurality of notches 28. As shown, a pair of these notches 28 are disposed individually to opposite surfaces 221, 222 of the second protrusion 22, where these two surfaces 221, 222 are parallel to the axial direction F1 of the pin 30. In addition, another pair of these notches 28 are disposed individually to the opposite seventh and eighth surfaces 213, 214 at corresponding positions between the fourth protrusion 23 and the corresponding second grooves 27.

The notches 18, 28 shown in FIG. 3A to FIG. 4B can be used to contain metals for development in a surgery, such as tantalum alloy, titanium alloy, pure titanium. Thereupon, during a surgery, the positions of the first protrusion 12, the second protrusion 13, the third protrusion 22 and the fourth protrusion 23 can be easily identified.

Figures 5A, 5B:
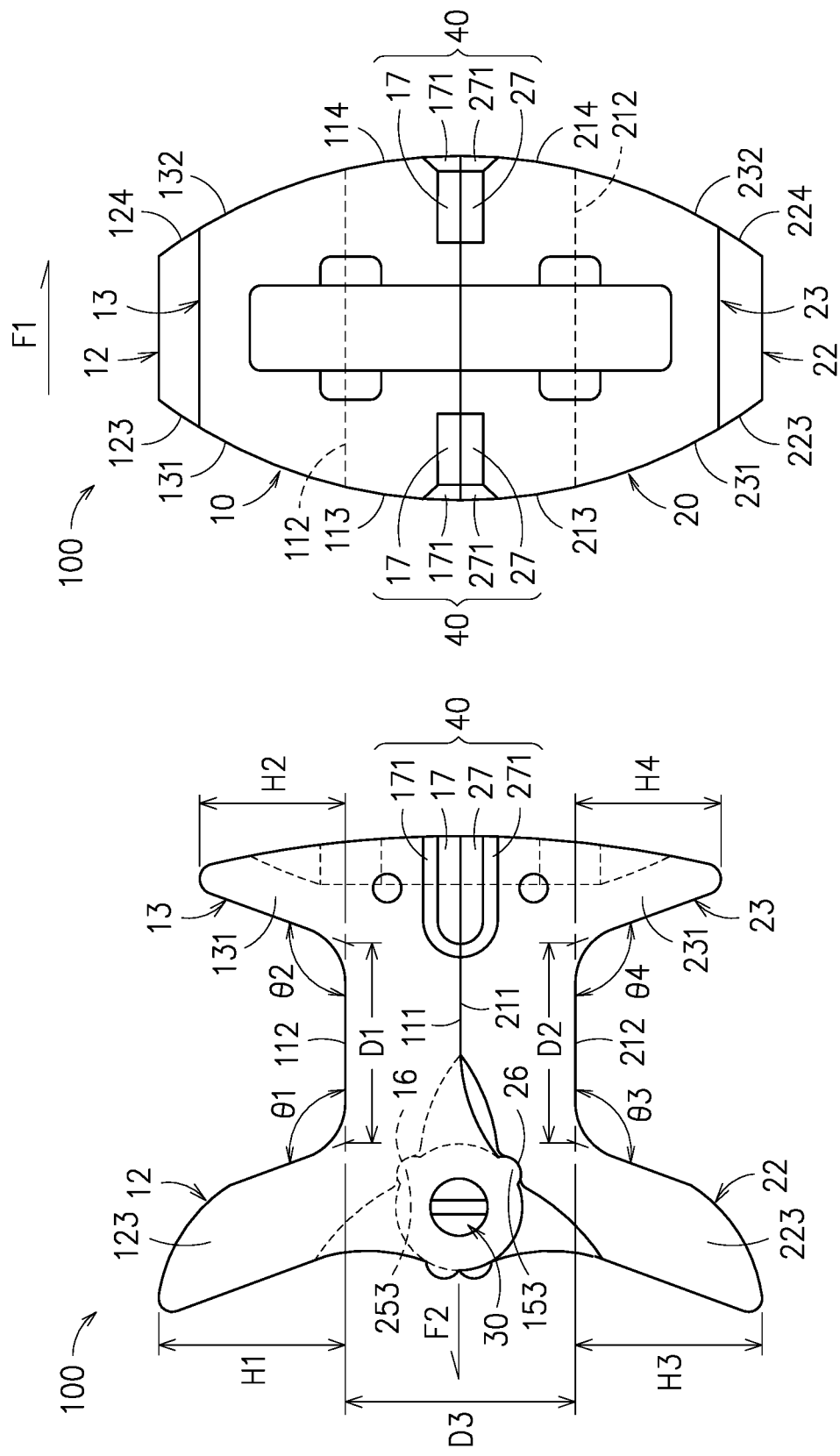
FIG. 5A is a schematic front view of FIG. 1.
FIG. 5B is a schematic right-side view of FIG. 5A.

Referring to FIG. 5A, a length H1 of the first protrusion 12 over the second surface 112 is greater than a length H2 of the second protrusion 13 over the second surface 112. In addition, a length H3 of the third protrusion 22 over the fourth surface 212 is greater than a length H4 of the fourth protrusion 24 over the fourth surface 212.

In this embodiment, a length H1 of the first protrusion 12 over the second surface 112 is equal to a length H3 of the third protrusion 22 over the fourth surface 212. In addition, a length H2 of the second protrusion 13 over the second surface 112 is equal to a length H4 of the fourth protrusion 24 over the fourth surface 212.

As shown, a first angle $\theta 1$ is formed between the first protrusion 12 and the second surface 112, a second angle $\theta 2$ is formed between the second protrusion 13 and the second surface 112, a third angle $\theta 3$ is formed between the third protrusion 22 and the fourth surface 212, and a fourth angle $\theta 4$ is formed between the fourth protrusion 24 and the fourth surface 212. In this embodiment, each of the first angle $\theta 1$, the second angle $\theta 2$, the third angle and $\theta 3$ and the fourth angle $\theta 4$ is greater than 90°. In particular, the first angle $\theta 1$ is equal to the third angle $\theta 3$, and the second angle $\theta 2$ is equal to the fourth angle $\theta 4$.

Referring to FIG. 2 to FIG. 5A, the first supporter 10 further includes two first pivotal-hole protrusions 15 and a first concave positioning portion 16.

The first pivotal-hole protrusions 15 are individually protruded from the first surface 111 by opposing the first protrusion 12. Each of the first pivotal-hole protrusions 15 is furnished with a first hole 151. In addition, the first pivotal-hole protrusion 15 has a first round end 152 concentric with the first hole 151.

One of the two first round ends 152 of the corresponding first pivotal-hole protrusions 15 has a curve surface furnished with a first positioning protrusion 153 and a second positioning protrusion 154. The first positioning protrusion 153 and the second positioning protrusion 154 are separately distributed on the curve surface concentric with the first hole 151.

Each of the first positioning protrusion 153 and the second positioning protrusion 154 is formed as an elongated strip having a semi-circular cross section. A longitudinal direction of the first positioning protrusion 153 or the second positioning protrusion 154 is parallel to the axial direction F1 of the pin 30.

The first concave positioning portion 16 is disposed at the first body 11 at one side of the first pivotal-hole protrusion 15. The first concave positioning portion 16 is also formed as an elongated strip having a semi-circular cross section, and a longitudinal direction of the first concave positioning portion 16 is parallel to the axial direction F1 of the pin 30.

The first body 11 has a surface of the first concave positioning portion 16 to be a first concave arc surface 115.

Referring to FIG. 2 to FIG. 5A, second supporter 20 further includes the second supporter 20 further includes two second pivotal-hole protrusions 25 and a second concave positioning portion 26.

The second pivotal-hole protrusions 25 are individually protruded from the third surface 211 by opposing the third protrusion 22. Each of the second pivotal-hole protrusions 25 is furnished with a second hole 251. In addition, the second pivotal-hole protrusion 25 has a second round end 252 concentric with the second hole 251.

One of the two second round ends 252 of the corresponding second pivotal-hole protrusion 25 has a curve surface furnished with a third positioning protrusion 253 and a fourth positioning protrusion 254. The third positioning protrusion 253 and the fourth positioning protrusion 254 are separately distributed on the curve surface concentric with the second hole 251.

Each of the third positioning protrusion 253 and the fourth positioning protrusion 254 is formed as an elongated strip having a semi-circular cross section. A longitudinal direction of the third positioning protrusion 253 or the fourth positioning protrusion 254 is parallel to the axial direction F1 of the pin 30.

The second concave positioning portion 26 is disposed at the second body 21 at one side of the second pivotal-hole protrusion 25. The second concave positioning portion 26 is also formed as an elongated strip having a semi-circular cross section, and a longitudinal direction of the second concave positioning portion 26 is parallel to the axial direction F1 of the pin 30.

The second body 21 has a surface of the second concave positioning portion 26 to be a second concave arc surface 215.

The first concave arc surface 115 and the second round end 252 of the second pivotal-hole protrusion 25 are to present a non-interference fit. Also, the second concave arc surface 215 and the first round end 152 of the first pivotal-hole protrusion 15 are to present another non-interference fit.

In this embodiment, the first supporter 10 has two first pivotal-hole protrusions 15, the second supporter 20 has two second pivotal-hole protrusions 25, and the two first pivotal-hole protrusions 15 and the two second pivotal-hole protrusions 25 are arranged at intervals, such that the pin 30 can pass through the first holes 151 of the corresponding first pivotal-hole protrusions 15 of the first supporter 10 and the second holes 251 of the corresponding second pivotal-hole protrusions 25 of the second supporter 20.

Referring to FIG. 5A and FIG. 5B, with respect to a radial direction F2 of the pin 30, the first supporter 10 and the second supporter 20 are symmetrically arranged. The first supporter 10 and the second supporter 20 are pivotally rotated to each other about the pin 30 in the axial direction F1, such that the device for expanding spacing between spinous processes 100 can present an expansion state and a close state. For example, in FIG. 5A and FIG. 5B, the close state of the device for expanding spacing between spinous processes 100 is demonstrated.

Referring to FIG. 5A and FIG. 5B, a distance D1 between the first protrusion 12 and the second protrusion 13 is ranged within 2~10 mm. In this embodiment, a distance D3 between the third protrusion 22 and the fourth protrusion 23 is equal to the distance D1 between the first protrusion 12 and the second protrusion 13, but not limited thereto. In addition, the pair of the third protrusion 22 and the fourth protrusion 23 are symmetric to the pair of the first protrusion 12 and the second protrusion 13 with respect to the radial direction of the pin 30, but not limited thereto.

Refer to FIG. 5A and FIG. 5B. While the device for expanding spacing between spinous processes 100 is in the close state as shown in FIG. 5A, the first surface 111 of the first supporter 10 is contacted with the third surface 211 of the second supporter 20, and each of the first grooves 17 is connected with the corresponding second groove 27 for forming together a lengthy groove 40. At the same time, by providing the first chamfered edges 171 and the second chamfered edges 271, two opposite pry points for breaking the close state of the device for expanding spacing between spinous processes 100 can be formed.

Referring to FIG. 5A, as the device for expanding spacing between spinous processes 100 is in the close state, the first surface 111, the second surface 112, the third surface 211 and the fourth surface 212 are all parallel to each other, the first surface 111 and the third surface 211 are contacted to each other, the first positioning protrusion 153 is snapped to the second concave positioning portion 26, and the third positioning protrusion 253 is snapped to the first concave positioning portion 16. However, in this embodiment, the distance D3 between the second surface 112 and the fourth surface 212 is not specifically defined, but determined according to practical spacing between the spinous processes; for example, a range of 8~16 mm for D3.

Refer to FIG. 5B. While the device for expanding spacing between spinous processes 100 is in the close state as shown in FIG. 5B, the fifth surface 113, the seventh surface 213, the surface 131 of the second protrusion 13, the surface 123 of the first protrusion 12, the surface 231 of the fourth protrusion 23, and the surface 223 of the third protrusion 22 are integrated to form an arc; the sixth surface 114, the eighth surface 214, the surface 124 of the first protrusion 12, the surface 224 of the third protrusion 22, the surface 132 of the second protrusion 13, and the surface 232 of the fourth protrusion 23 are integrated to form another arc; and, these two arcs are symmetrically arranged.

Figure 6B:
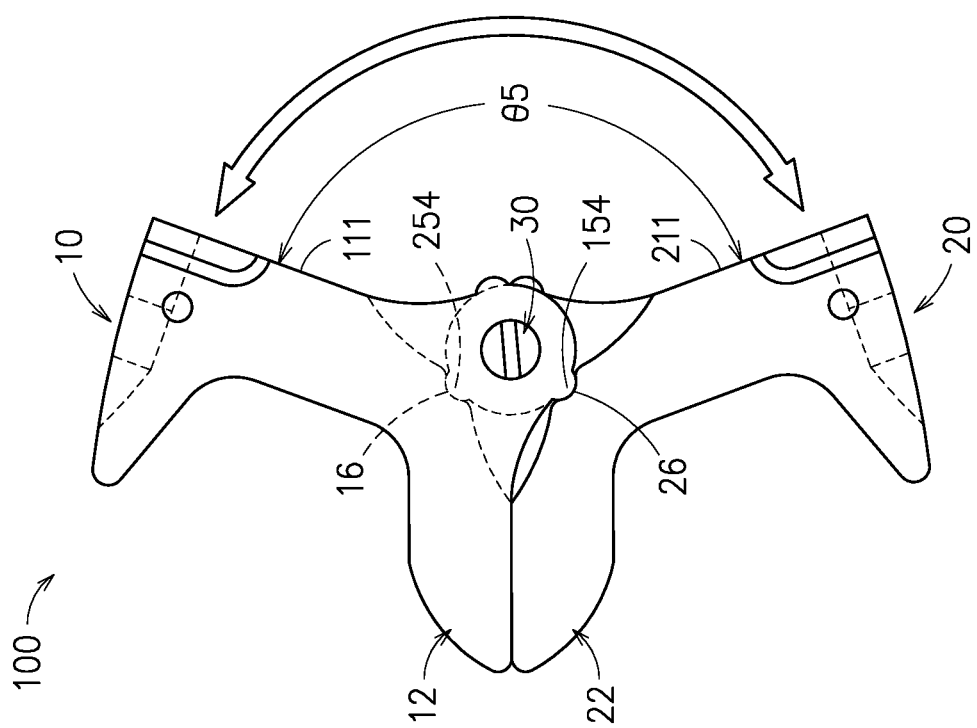
FIG. 6B demonstrates schematically an expansion state of the device of FIG. 1.
Figure 6A:
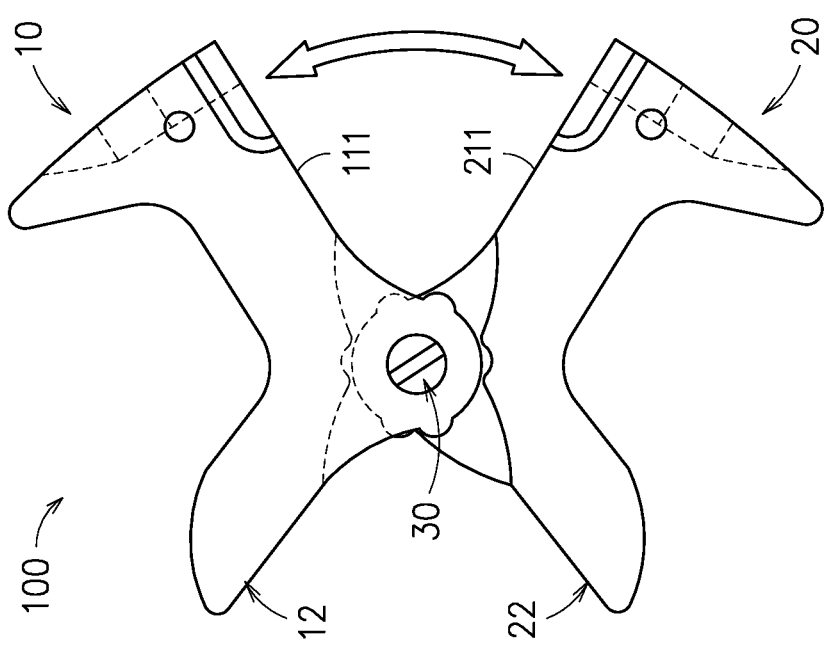
FIG. 6A demonstrates schematically a middle state of the device of FIG. 1 from a close state shown in FIG. 1.

Referring to FIG. 5A, FIG. 6A and FIG. 6B, different states of the device for expanding spacing between spinous processes 100 from the close state to the expansion state are schematically demonstrated.

In FIG. 5A, the device for expanding spacing between spinous processes 100 is in the close state, in which the first surface 111 of the first supporter 10 is contacted with the third surface 211 of the second supporter 20 (also, see FIG. 1).

In FIG. 6A, the first supporter 10 and the second supporter 20 are turned pivotally about the pin 30 so as to separate the first surface 111 of the first supporter 10 from the third surface 211 of the second supporter 20, and to move the first protrusion 12 of the first supporter 10 closer to the third protrusion 22 of the second supporter 20.

Figure 7:
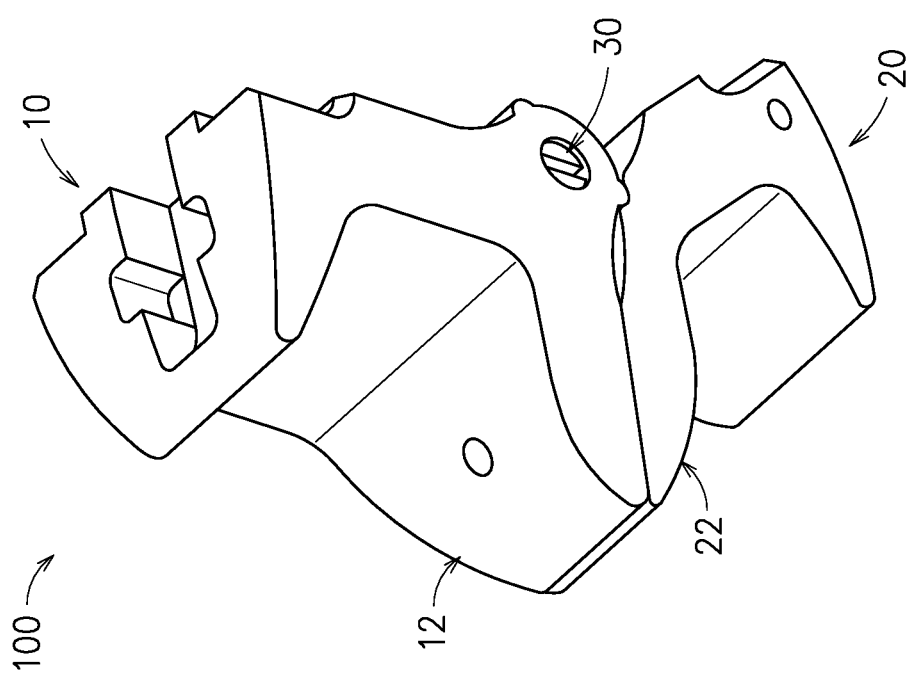
FIG. 7 is another schematic perspective view of FIG. 1, where the device is in the expansion state.

In FIG. 6B, the first supporter 10 and the second supporter 20 are further turned pivotally about the pin 30 till the first protrusion 12 of the first supporter 10 and the third protrusion 22 of the second supporter 20 are contacted to each other, the second positioning protrusion 154 is snapped onto the second concave positioning portion 26, and the fourth positioning protrusion 253 is snapped onto the first concave positioning portion 16, then the device for expanding spacing between spinous processes 100 reaches the expansion state (see also FIG. 7).

Referring to FIG. 6B, a fifth angle θ5 is formed between the first surface 111 of the first supporter 10 and the third surface 211 of the second supporter 20. In this embodiment, the range of the fifth angle θ5 is not specifically limited, but per practical needs; for example, a range of 100~180°.

Via the aforesaid pivotal motions about the pin 30, the device for expanding spacing between spinous processes 100 can be switched from the close state to the expansion state. While in the expansion state, the device for expanding spacing between spinous processes 100 can be inserted between the spinous processes.

Referring to FIG. 6B, FIG. 8A to FIG. 8C, and FIG. 9, a method for expanding spacing between spinous processes 300 by applying the device for expanding spacing between spinous processes 100 can include the following steps.

Step 302: Rotate pivotally the first supporter 10 away from the second supporter 20 by having the pin 30 as a pivotal shaft so as to have the first protrusion 12 to contact the third protrusion 22. At this time, the device for expanding spacing between spinous processes 100 is posed in the expansion state, as shown in FIG. 6B.

Figure 8A:
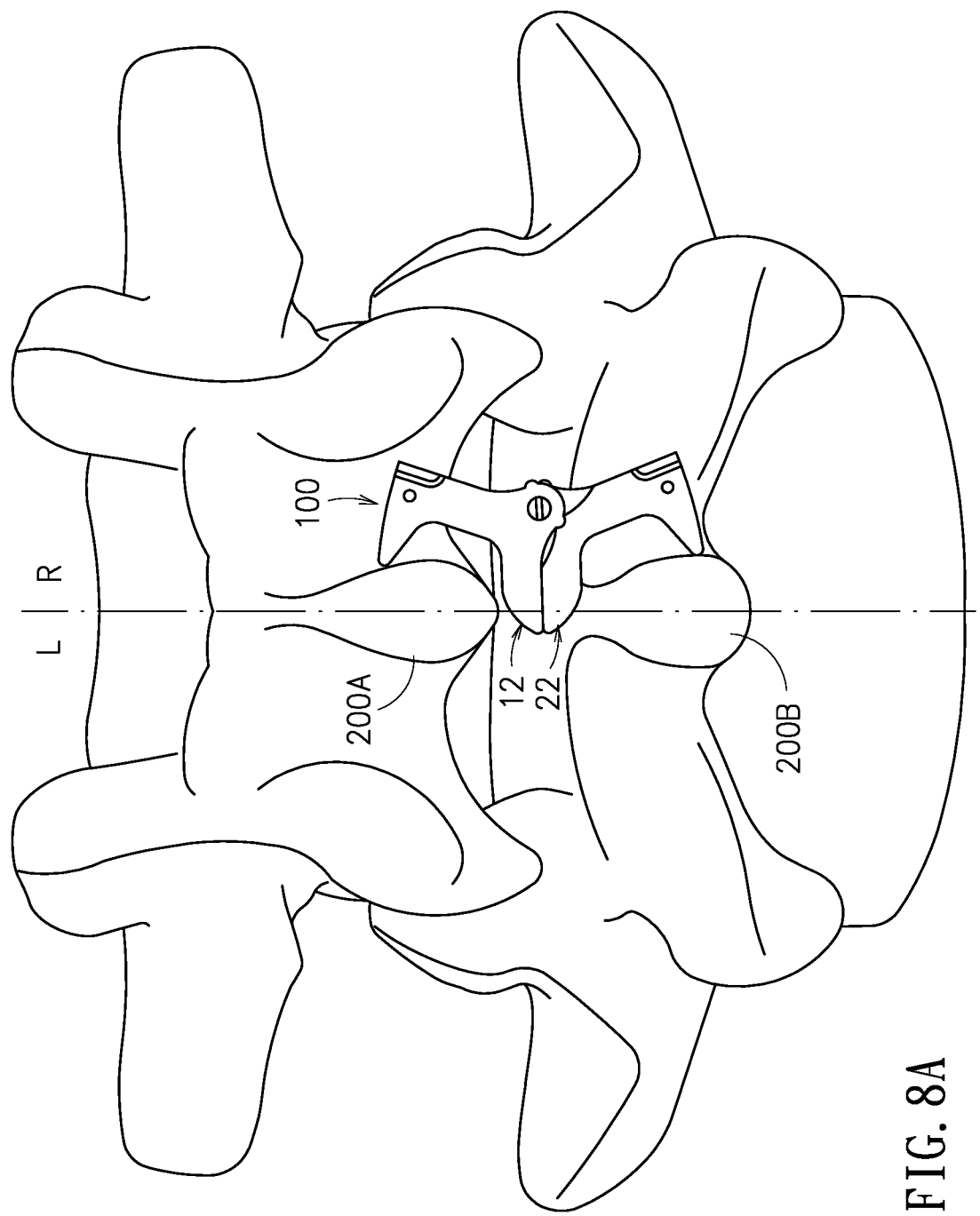
FIG. 8A to FIG. 8C demonstrate schematically different states of FIG. 1, while being installed between two spinous processes.

Step 304: Insert the first protrusion 12 and the third protrusion 22 of the device for expanding spacing between spinous processes 100 into a space between the two spinous processes 200A, 200B from a side R of the two spinous processes 200A, 200B, as shown in FIG. 8A.

Figure 8B:
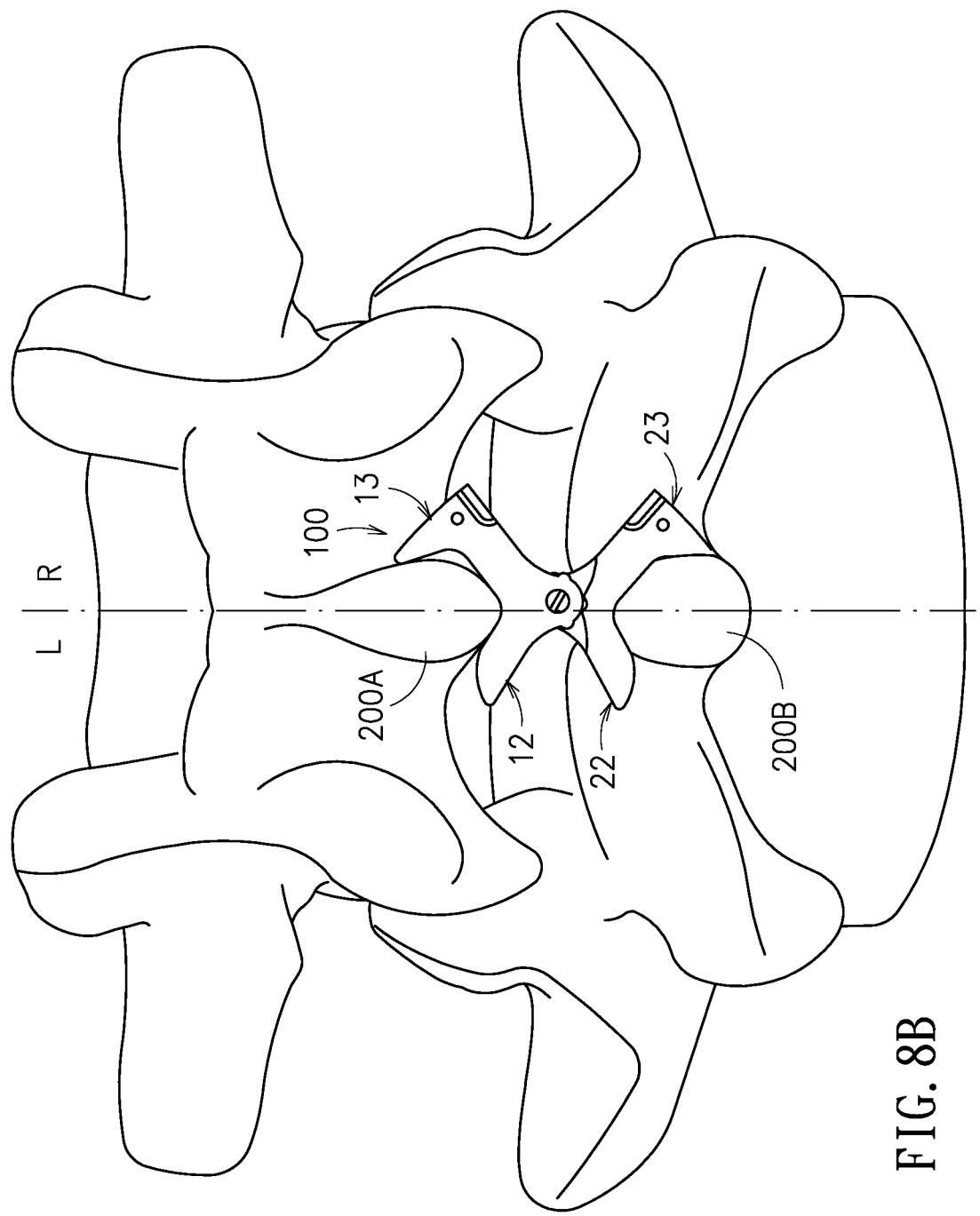

Step 306: Push the device for expanding spacing between spinous processes 100 to have the first protrusion 12 and the third protrusion 22 to pass through the space between the two spinous processes 200A, 200B and then to reach another side L of the two spinous processes 200A, 200B, such that the first supporter 10 and the second supporter 20 are pivoted to contact each other about the pin 30, as shown in FIG. 8B.

While in pushing the device for expanding spacing between spinous processes 100 from the side R of the two spinous processes 200A, 200B to the other side L thereof, the second protrusion 13 and the fourth protrusion 23 would move along the two spinous processes 200A, 200B to contact each other, and simultaneously the first protrusion 12 and the third protrusion 22 are separated to each other.

Step 308: Have the first surface 111 of the first supporter 10 to contact the third surface 211 of the second supporter 20, and thus to pose the device for expanding spacing between spinous processes 100 in a close state, so that the first protrusion 12 and the third protrusion 22 are disposed at one side L of the two spinous processes 200A, 200B, and the second protrusion 13 and the fourth protrusion 23 at another side R of the two spinous processes 200A, 200B opposing the side L. At this time, the first concave portion 14 and the second concave portion 24 are disposed between the two spinous processes 200A, 200B, as shown in FIG. 8C.

Upon such an arrangement, the device for expanding spacing between spinous processes 100 can be positioned between the two spinous processes 200A, 200B. At this time, the first concave portion 14 and the second concave portion 24 provide rooms for supporting the two spinous processes 200A, 200B, respectively, and the first protrusion 12, the third protrusion 22, the second protrusion 13 and the fourth protrusion 23 are there to prevent the device for expanding spacing between spinous processes 100 from further movements.

Figure 10A:
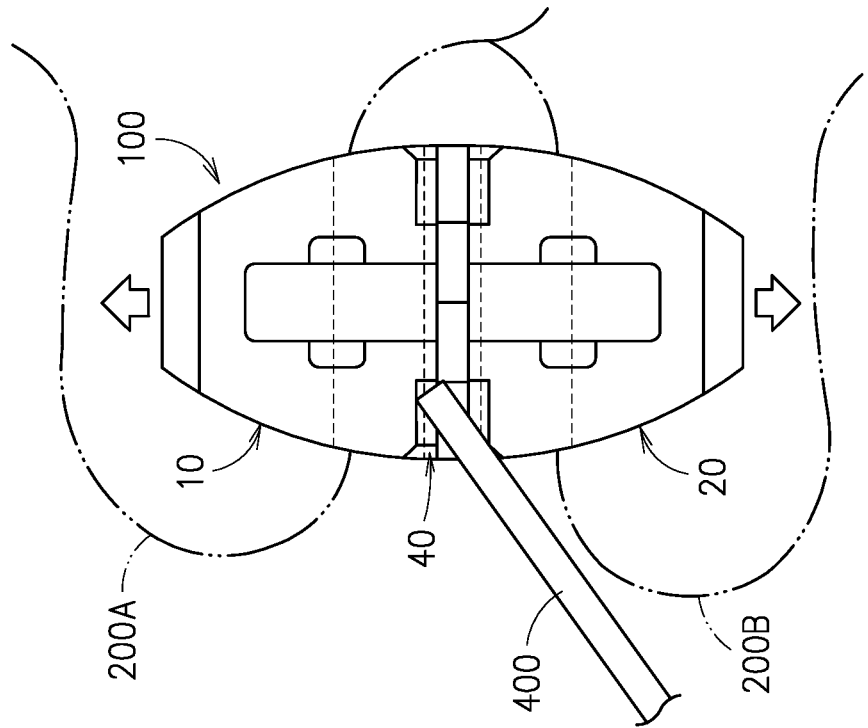
FIG. 10A and FIG. 10B demonstrate schematically two states of FIG. 1, while a tool is used to open the device.
Figure 10B:
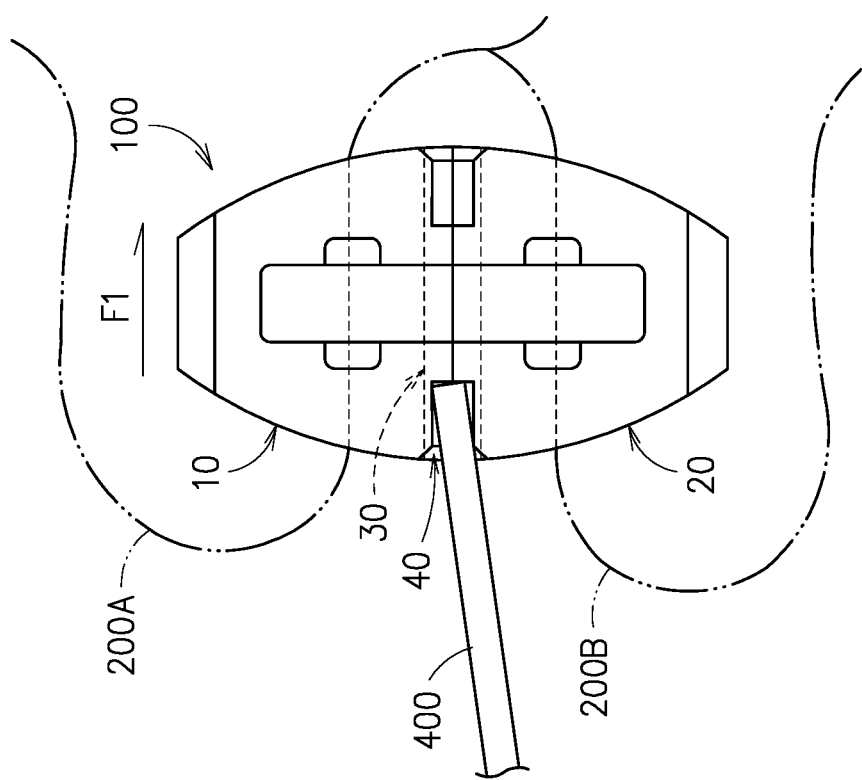

Referring to FIGS. 10A and 10B, while the device for expanding spacing between spinous processes 100 is to be removed away from the two spinous processes 200A, 200B, a lengthy tool 400 can be applied.

Figure 8C:
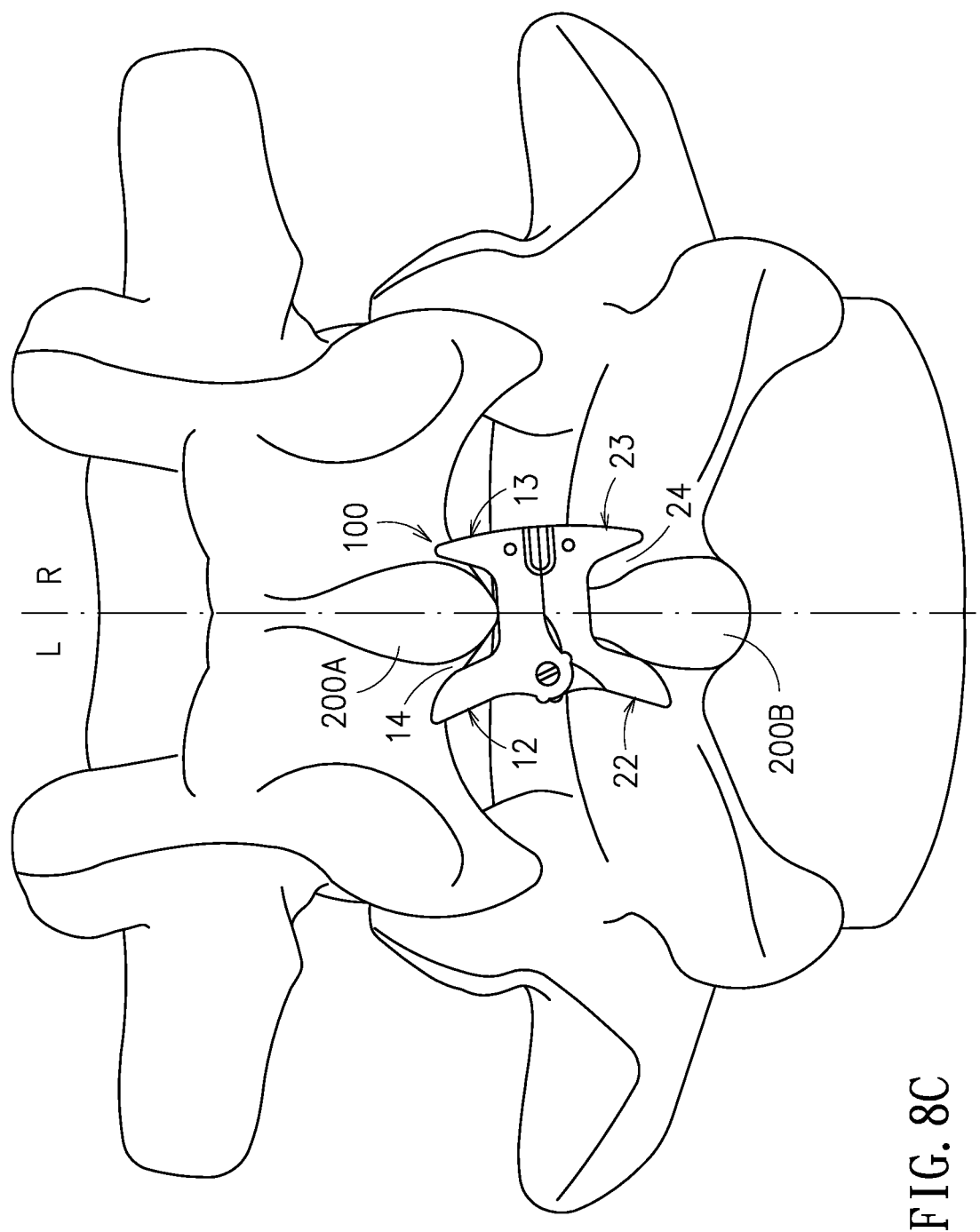
Figure 9:
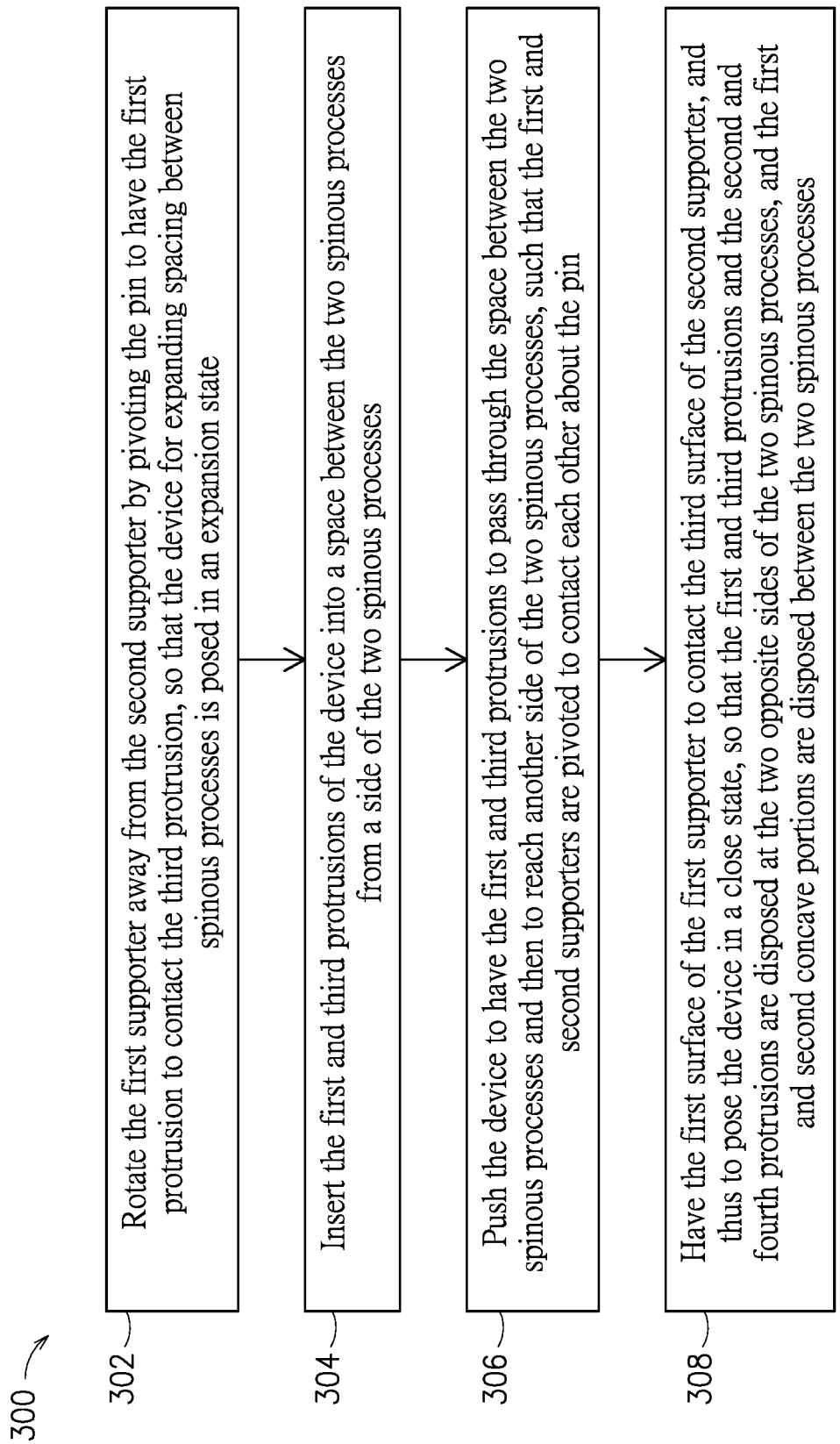
FIG. 9 is a schematic flowchart of an embodiment of the method for expanding spacing between spinous processes in accordance with this disclosure.

As shown in FIG. 10A, the tool 400 pierces loosely into the lengthy groove 40 in a manner roughly parallel to the axial direction F1 of the pin 30, while the device for expanding spacing between spinous processes 100 is in a state as shown in FIG. 8C. Then, as shown in FIG. 10B, the tool 400 is depressed to pivotally separate the first supporter 10 from the second supporter 20 about the pin 30, while the device for expanding spacing between spinous processes 100 is in a state as shown in FIG. 8B. Thus, the device for expanding spacing between spinous processes 100 can be switched from the close state of FIG. 8C, to a transition state of FIG. 8B, and finally to the expansion state of FIG. 8A. Then, the device for expanding spacing between spinous processes 100 can be removed.

Figure 11:
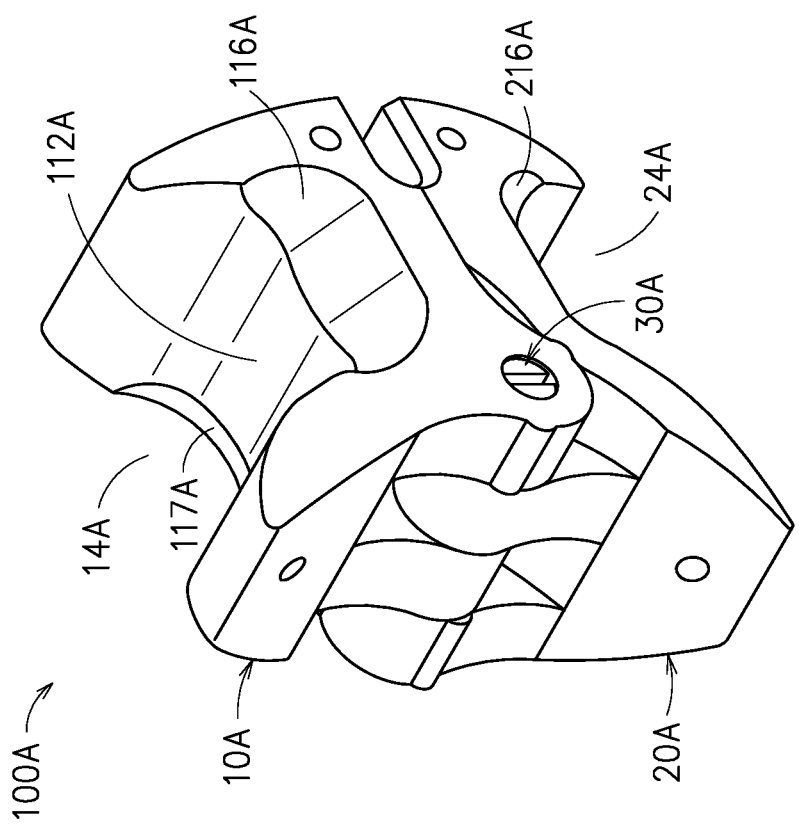
FIG. 11 is a schematic perspective view of another embodiment of the device for expanding spacing between spinous processes in accordance with this disclosure.

Referring to FIG. 11, FIG. 11A and FIG. 11B, another embodiment of the device for expanding spacing between spinous processes 100A includes a first supporter 10A, a second supporter 20A and a pin 30A. In this embodiment, the first supporter 10A, the second supporter 20A and the pin 30A are structured roughly the same as those of the embodiment shown in FIG. 1, but major differences in between are that, in this embodiment, third chamfered edges 116A, 117A are individually provided to connect the second surface 112A to the fifth surface 113A, and the second surface 112A to the sixth surface 114A, respectively, at the first supporter 10A; and, fourth chamfered edges 216A, 217A are individually provided to connect the fourth surface 212A to the seventh surface 213A, and the fourth surface 212A to the eighth surface 214A, respectively, at the second supporter 20A. As a result, by having the third chamfered edges 116A, 117A to pair the first concave portion 14A and the fourth chamfered edges 216A, 217A to pair the second concave portion 24A, a "quasi-saddle shape" can be formed.

Figure 12:
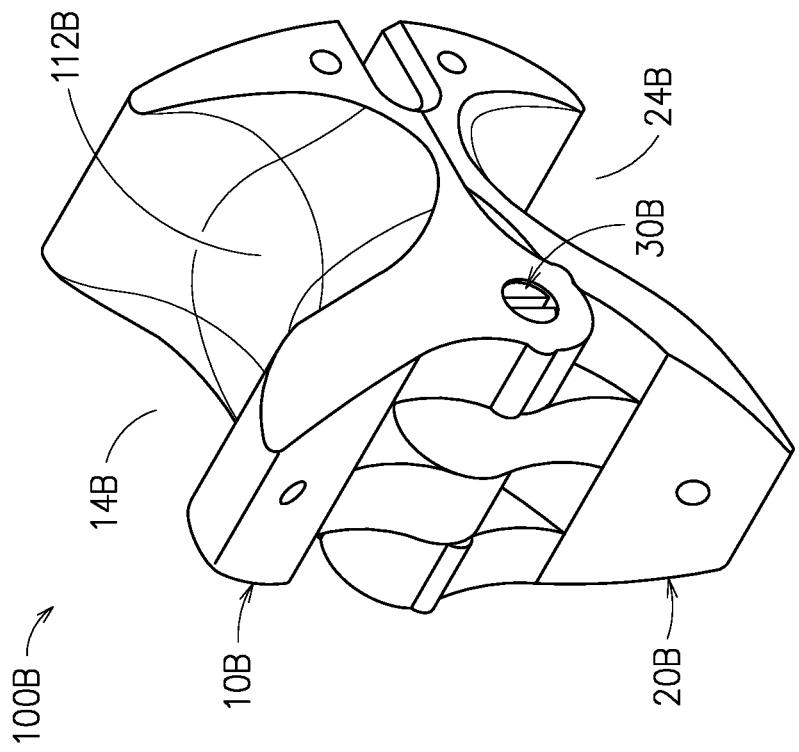
FIG. 12 is a schematic perspective view of a further embodiment of the device for expanding spacing between spinous processes in accordance with this disclosure.
Figure 12B:
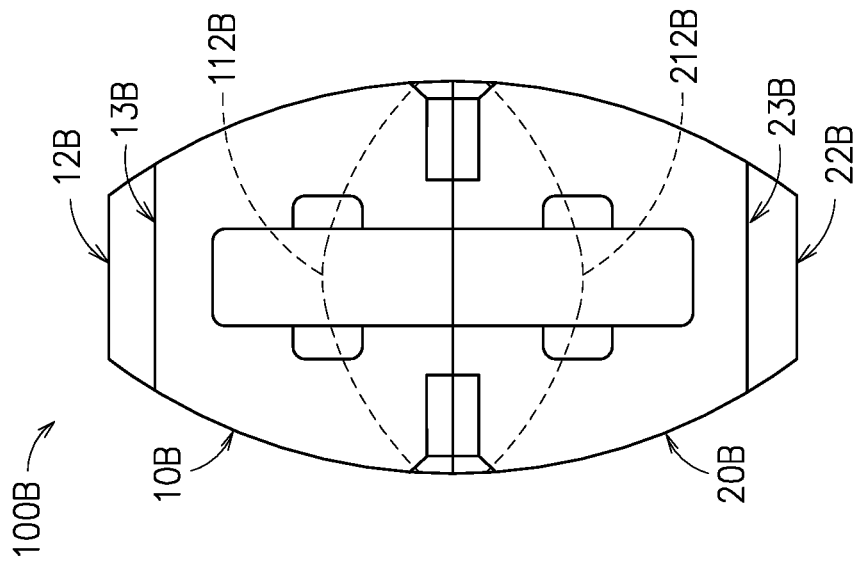
FIG. 12B is a schematic right-side view of FIG. 12.
Figure 12A:
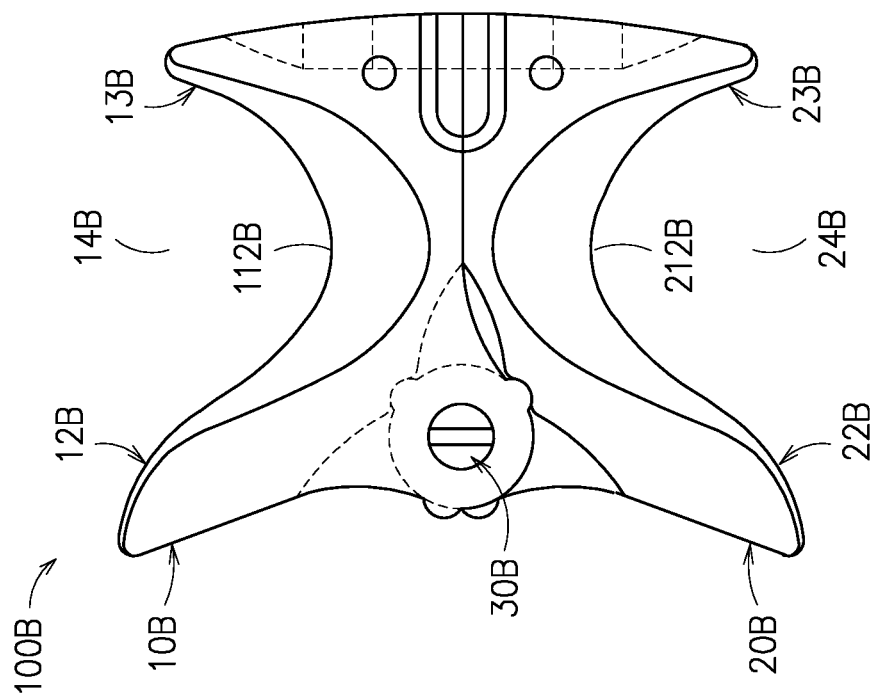
FIG. 12A is a schematic front view of FIG. 12.

Referring to FIG. 12, FIG. 12A and FIG. 12B, a further embodiment of the device for expanding spacing between spinous processes 100B includes a first supporter 10B, a second supporter 20B and a pin 30B. In this embodiment, the first supporter 10B, the second supporter 20B and the pin 30B are structured roughly the same as those of the embodiment shown in FIG. 1, but major differences in between are that, in this embodiment, the second surface 112B, the first protrusion 12B and the second protrusion 13B of the first supporter 10B are smoothly connected to form a smooth saddle shape, and the fourth surface 212B, the third protrusion 22B and the fourth protrusion 23B of the second supporter 20B are smoothly connected to form another smooth saddle shape.

In this disclosure, though different embodiments are provided in FIG. 1, FIG. 11 and FIG. 12, yet the only difference lies on slight structural changes at the first concave portion and the second concave portion, and options of the embodiments are up to the practical formation of the spinous processes.

In addition, in any embodiment of the device for expanding spacing between spinous processes 100, 100A or 100B shown in FIG. 1, FIG. 11 or FIG. 12, the first supporter 10, 10A or 10B and the second supporter 20, 20A or 20B are symmetrically arranged with respect to the radial direction F2 of the pin 30, 30A or 30B. However, in any of the device for expanding spacing between spinous processes 100, 100A or 100B, the first supporter 10, 10A or 10B and the second supporter 20, 20A or 20B may be matched to form a mechanism that the first supporter and the second supporter are not symmetrically arranged with respect to the radial direction of the pin, such that the two spinous processes with different configurations can be served.

Figure 13C:
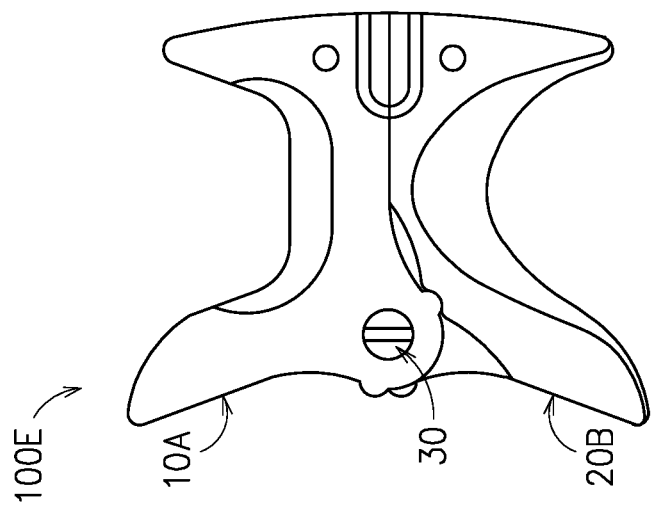
FIG. 13A to FIG. 13C demonstrate schematically different pairing of the first supporter and the second supporter in FIG. 1, FIG. 11 and FIG. 12, respectively.
Figure 13B:
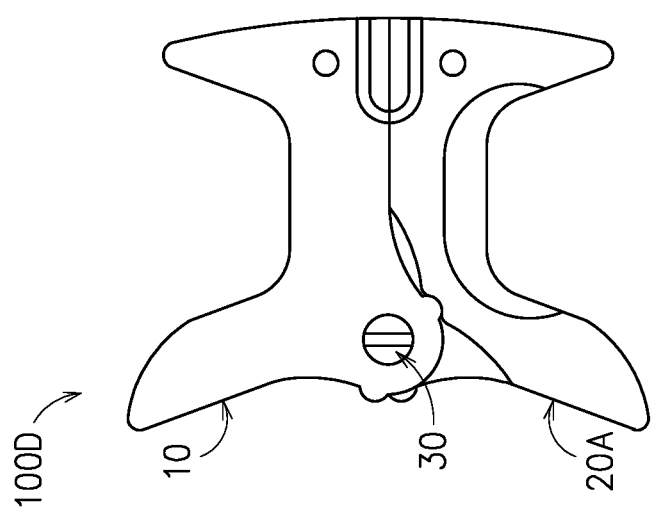
Figure 13A:
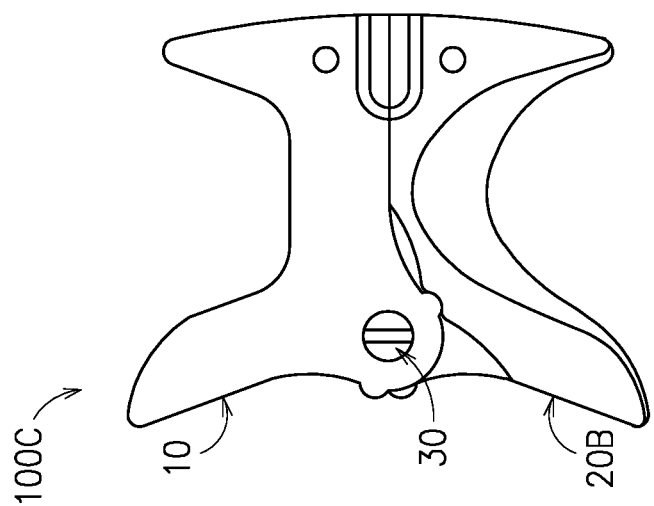

Refer to FIG. 13A to FIG. 13C; where the device for expanding spacing between spinous processes 100C of FIG. 13A is provided by integrating the first supporter 10, the second supporter 20B and the pin 30 to form an asymmetric structure, the device for expanding spacing between spinous processes 100D of FIG. 13B is provided by integrating the first supporter 10, the second supporter 20A and the pin 30 to form another asymmetric structure, and the device for expanding spacing between spinous processes 100E of FIG. 13C is provided by integrating the first supporter 10A, the second supporter 20B and the pin 30 to form a further asymmetric structure.

In any of the embodiments shown in FIGS. 1, 11, 12 and 13A-13C, the device for expanding spacing between spinous processes 100, 100A, 100B, 100C, 100D or 100E is identically operated, referring to FIG. 8A to FIG. 8C for an installation between two spinous process, and to FIG. 10A to FIG. 10B for applying a tool to remove the device.

In summary, in the device for expanding spacing between spinous processes provided by this disclosure, with pivotal motion between the first supporter and the second supporter, various advantages such as simple structuring, easy operation, convenience in both installation and removal, ability to retain the ligament of spinous process, cone stability, and a significant reduce in the risk of bleeding and infection can be obtained, while a surgery needs the spinous process to be supported.

With respect to the above description then, it is to be realized that the optimum dimensional relationships for the parts of the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present disclosure.

What is claimed is:

1. A device for expanding spacing between spinous processes, comprising:
    a first supporter, including:
        a first body, having oppositely a first surface and a second surface;
        a first protrusion, protruding at one side of the second surface;
        a second protrusion, protruding at another side of the second surface by opposing the first protrusion;
        a first concave portion, formed among the second surface, the first protrusion and the second protrusion;
        at least one first pivotal-hole protrusion, disposed on the first surface by opposing the first protrusion, each of the at least one first pivotal-hole protrusion being furnished with a first hole, a surface of one of the at least one first pivotal-hole protrusion being furnished thereon with a first positioning protrusion and a second positioning protrusion, the surface being concentric with the first hole; and at least one first concave positioning portion, disposed on the first body in a side of the at least one first pivotal-hole protrusion;
    a second supporter, including:
        a second body, having oppositely a third surface and a fourth surface;
        a third protrusion, protruding at one side of the fourth surface;
        a fourth protrusion, protruding at another side of the fourth surface by opposing the third protrusion;
        a second concave portion, formed among the fourth surface, the third protrusion and the fourth protrusion;
        at least one second pivotal-hole protrusion, disposed on the third surface by opposing the third protrusion, each of the at least one second pivotal-hole protrusion being furnished with a second hole, a surface of one of the at least one second pivotal-hole protrusion being furnished thereon with a third positioning protrusion and a fourth positioning protrusion, the surface being concentric with the second hole; and
        at least one second concave positioning portion, disposed on the second body in a side of the at least one second pivotal-hole protrusion; and
    a pin, disposed pivotally at the first supporter and the second supporter, the first supporter and the second supporter pivoting about the pin to provide the device for expanding spacing between spinous processes an expansion state and a close state; wherein, while the device for expanding spacing between spinous processes is in the expansion state, the first protrusion and the third protrusion are contacted to each other; wherein, while the device for expanding spacing between spinous processes is in the close state, the first surface and the third surface are contacted to each other;
    wherein, when the device for expanding spacing between spinous processes is in the close state, the first positioning protrusion is snapped to the at least one second concave positioning portion, and the third positioning protrusion is snapped on the at least one first concave positioning portion;
    wherein, when the device for expanding spacing between spinous processes is in the expansion state, the first protrusion and the third protrusion are contacted to each other, the second positioning protrusion is snapped to the at least one second concave positioning portion, and the fourth positioning protrusion is snapped to the at least one first concave positioning portion.

2. The device for expanding spacing between spinous processes of claim 1, wherein each of the first positioning protrusion, the second positioning protrusion, the third positioning protrusion and the fourth positioning protrusion is formed as a strip having a semi-circular cross section; a width direction of any of the first positioning protrusion, the second positioning protrusion, the third positioning protrusion and the fourth positioning protrusion is parallel to an axial direction of the pin, each of the first concave positioning portion and the second concave positioning portion is formed as a strip having a semi-circular cross section; and, another width direction of any of the first concave positioning portion and the second concave positioning portion is parallel to the axial direction of the pin.

3. The device for expanding spacing between spinous processes of claim 1, wherein the first pivotal-hole protrusion has a first round end concentric with the first hole, the first positioning protrusion and the second positioning protrusion are disposed on a surface of the first round end, the second pivotal-hole protrusion has a second round end concentric with the second hole, and the third positioning protrusion and the fourth positioning protrusion are disposed on another surface of the second round end.

4. The device for expanding spacing between spinous processes of claim 1, wherein the first supporter has two said first pivotal-hole protrusions, the second supporter has two said second pivotal-hole protrusions, and the two first pivotal-hole protrusions and the two second pivotal-hole protrusions are arranged at intervals.

5. The device for expanding spacing between spinous processes of claim 1, wherein:
    the first supporter further includes two first grooves, the two first grooves being disposed at another side of the first body with respect to the pin, parallel to an axial direction of the pin, and separated to two opposite corners of the first surface; and
    the second supporter further includes two second grooves, the two second grooves being disposed at another side of the second body with respect to the pin, parallel to the axial direction of the pin, and separated to two opposite corners of the third surface;
    wherein, when the device for expanding spacing between spinous processes is in the close state, each of the first grooves is connected with the corresponding second groove to form a lengthy groove, the lengthy groove is to receive a tool loosely in a direction roughly parallel to the axial direction of the pin, and the first supporter and the second supporter are pivotally separated by depressing the tool pivotally about the pin so as to pose the device for expanding spacing between spinous processes in the expansion state.

6. The device for expanding spacing between spinous processes of claim 1, wherein a length of the first protrusion over the second surface is greater than a length of the second protrusion over the second surface, and a length of the third protrusion over the fourth surface is greater than a length of the fourth protrusion over the fourth surface.

7. The device for expanding spacing between spinous processes of claim 1, wherein a length of the first protrusion over the second surface is equal to a length of the third protrusion over the fourth surface, and a length of the second protrusion over the second surface is equal to a length of the fourth protrusion over the fourth surface.

8. The device for expanding spacing between spinous processes of claim 1, wherein a first angle is formed between the first protrusion and the second surface , a second angle is formed between the second protrusion and the second surface, a third angle is formed between the third protrusion and the fourth surface, a fourth angle is formed between the fourth protrusion and the fourth surface, and each of the first angle, the second angle, the third angle and the fourth angle is greater than 90°.

9. The device for expanding spacing between spinous processes of claim 8, wherein the first angle is equal to the third angle, and the second angle is equal to the fourth angle.

10. The device for expanding spacing between spinous processes of claim 1, wherein, when the device for expanding spacing between spinous processes is in the close state, the first surface, the second surface, the third surface and the fourth surface are parallel to each other.

11. The device for expanding spacing between spinous processes of claim 1, wherein each of the first protrusion and the second protrusion is protruded outward from the second surface in a tapering manner, and each of the third protrusion and the fourth protrusion is protruded outward from the fourth surface in another tapering manner.

12. The device for expanding spacing between spinous processes of claim 1, wherein each of the first protrusion and the second protrusion has a width ranged within 2~10 mm, and each of the third protrusion and the fourth protrusion has a width equal to the width of each of the first protrusion and the second protrusion.

13. The device for expanding spacing between spinous processes of claim 5, wherein the first body has oppositely a fifth surface and a sixth surface, the fifth surface and the sixth surface are disposed between the first surface and the second surface, the fifth surface and the sixth surface are roughly perpendicular to the first surface and the second surface; the second body has oppositely a seventh surface and an eighth surface, the seventh surface and the eighth surface are disposed between the third surface and the fourth surface, and the seventh surface and the eighth surface are roughly perpendicular to the third surface and the fourth surface.

14. The device for expanding spacing between spinous processes of claim 13, wherein each surface of the fifth surface, the sixth surface, the seventh surface, the eighth surface, opposite surfaces of the first protrusion parallel to the axial direction of the pin, and opposite surfaces of the third protrusion parallel to the axial direction of the pin is furnished with a notch for containing a metal for development.

15. The device for expanding spacing between spinous processes of claim 14, wherein the notch disposed on the fifth surface or the sixth surface is located between the second protrusion and one of the two first grooves, and the notch disposed on the seventh surface or the eighth surface is located between the fourth protrusion and one of the two second grooves.

16. The device for expanding spacing between spinous processes of claim 14, wherein the metal for development is one of tantalum alloy, titanium alloy and pure titanium.

17. The device for expanding spacing between spinous processes of The device for expanding spacing between spinous processes of claim 13, wherein third chamfered edges are provided to connect the second surface and the fifth surface and to connect the second surface and the sixth surface at the first supporter, fourth chamfered edges are provided to connect the fourth surface and the seventh surface and to connect the fourth surface and the eighth surface at the second supporter, the third chamfered edges and the first concave portion are integrated to form a quasi-saddle shape, and the fourth chamfered edges and the second concave portion are integrated to form another quasi-saddle shape.

18. The device for expanding spacing between spinous processes of claim 13, wherein a distance is formed between the fifth surface and the sixth surface, and the same distance is also formed between the seventh surface and the eighth surface; wherein, when the device for expanding spacing between spinous processes is in the close state, the fifth surface and the seventh surface are integrated to form a smooth surface, the sixth surface and the eighth surface are integrated to form a smooth surface, and the distance is ranged within 5~20 mm.

19. The device for expanding spacing between spinous processes of claim 1, wherein, when the device for expanding spacing between spinous processes is in the expansion state, a fifth angle is formed between the first surface and the third surface, and the fifth angle is ranged within 100~180°.

20. The device for expanding spacing between spinous processes of claim 1, wherein the second surface, the first protrusion and the second protrusion are integrated to form a smooth saddle shape at the first supporter, and the fourth surface, the third protrusion and the fourth protrusion are integrated to form another smooth saddle shape.

21. The device for expanding spacing between spinous processes of claim 1, wherein the first protrusion is roughly shaped as a trapezoid and is disposed at one side of the second surface, an end of the first protrusion away from the second surface is narrower, the second protrusion opposing the first protrusion is roughly shaped as another trapezoid and disposed at another side of the second surface, an end of the second protrusion away from the second surface is narrower, the third protrusion is roughly shaped as a trapezoid and is disposed at one side of the fourth surface, an end of the third protrusion away from the fourth surface is narrower, the fourth protrusion opposing the third protrusion is roughly shaped as another trapezoid and disposed at another side of the fourth surface, an end of the fourth protrusion away from the fourth surface is narrower.

22. The device for expanding spacing between spinous processes of claim 1, wherein the first supporter and the second supporter are radially symmetric with respect to the pin.

23. The device for expanding spacing between spinous processes of claim 1, wherein the first supporter and the second supporter are radially asymmetric with respect to the pin.

24. A method for expanding spacing between spinous processes, comprising the steps of:
   (a) preparing the device of claim 1;
   (b) turning the first supporter and the second supporter to have the first protrusion to contact the third protrusion, so that the first supporter and the second supporter are posed in an expansion state;
   (c) inserting the first protrusion of the first supporter and the third protrusion of the second supporter into a space between two spinous processes;
   (d) turning the first supporter and the second supporter to have the first surface contact the third surface, so that the first supporter and the second supporter are posed in a close state; and
   (e) having the first protrusion and the third protrusion disposed at a side of the two spinous processes, the second protrusion and the fourth protrusion disposed at another side of the two spinous processes, and the first concave portion and the second concave portion disposed between the two spinous processes.

* * * * *